United States Patent

Chalmers et al.

[11] Patent Number: 4,498,474
[45] Date of Patent: Feb. 12, 1985

[54] EPILATION METHOD

[76] Inventors: Edward Chalmers, 31 Benjamin Rd., Arlington, Mass. 02174; William H. Huggins, 26 Heritage Cir., Clinton, Conn. 06413

[21] Appl. No.: 361,630

[22] Filed: Mar. 25, 1982

Related U.S. Application Data

[63] Continuation-in-part of Ser. No. 344,494, Feb. 1, 1982, abandoned, which is a continuation of Ser. No. 42,799, May 29, 1979, Pat. No. 4,317,450.

[51] Int. Cl.³ .............................................. A61B 17/41
[52] U.S. Cl. ........................... 128/303.13; 128/303.17
[58] Field of Search ..................... 128/303.13, 303.17, 128/303.18, 639, 803

[56] References Cited

U.S. PATENT DOCUMENTS

| | | | |
|---|---|---|---|
| 2,886,564 | 5/1959 | Holysz | 128/639 X |
| 2,888,927 | 6/1959 | Fozard | 128/303.13 |
| 3,027,333 | 3/1962 | Friedman | 128/639 X |
| 3,567,657 | 3/1971 | Liehenstein | 128/639 X |
| 3,999,552 | 12/1976 | Huggins | 128/303.13 |
| 4,174,714 | 11/1979 | Mehl | 128/303.13 |
| 4,317,450 | 3/1982 | Chalmers et al. | 128/303.13 |

FOREIGN PATENT DOCUMENTS

WO80/02640 12/1980 World Intel. Prop. Org. ............................. 128/303.13

Primary Examiner—Lee S. Cohen

[57] ABSTRACT

An epilator system for removing hair, employing a wetting fluid with ionic properties. The ionic wetting fluid is applied to the hair down into the follicle to the papilla and preferably a high-frequency voltage lower than used in conventional epilators is then applied in the region of a wetted hair. The hair is drawn easily from the follicle, generally without regrowth. In preferred embodiments, two or more fluids are applied sequentially, the last having lower ionic activity, but preferably having activity equivalent to at least about 25 ppm sodium chloride in water solution. The ratio of ionic activity of the preceding fluid to the ionic activity of the final fluid is in the range of about 10:1 to 1:1, preferably about 5:1. Preferably the preceding fluid is applied to the skin, wiped leaving a deposit in the pore, and the last fluid is applied. An epilator fluid and epilator kit are also claimed.

22 Claims, 12 Drawing Figures

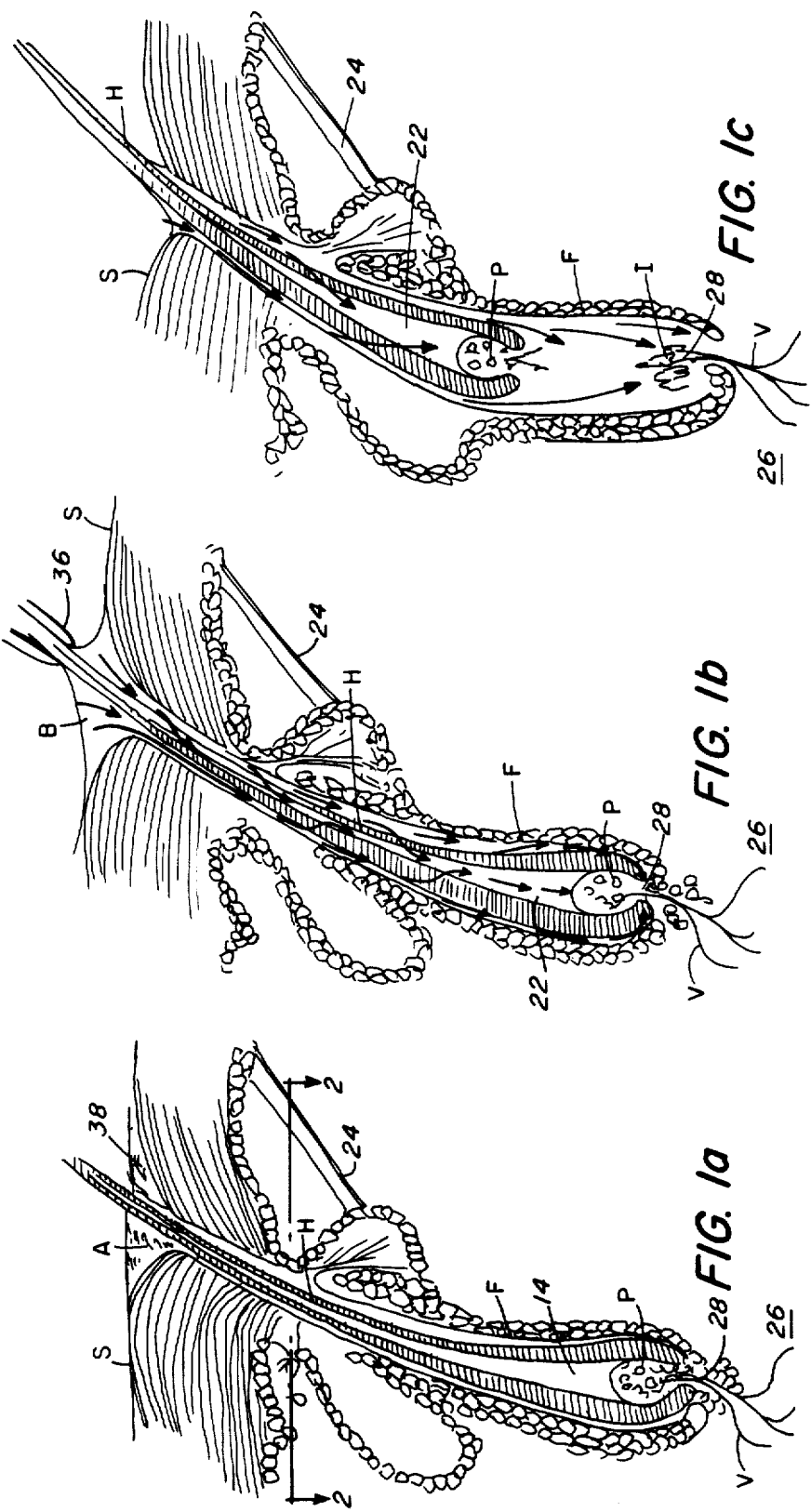

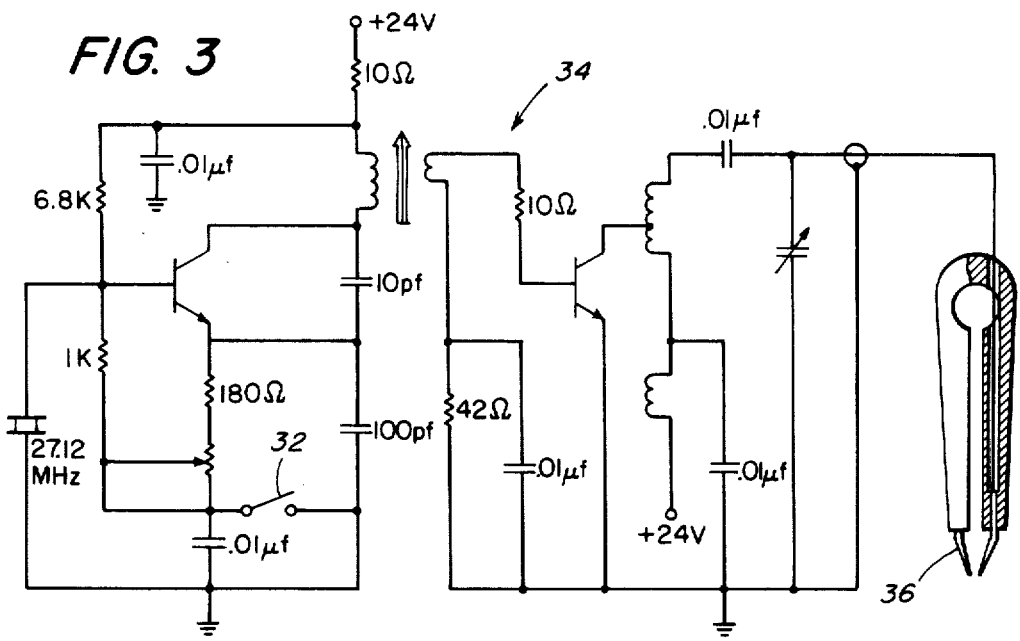
FIG. 3
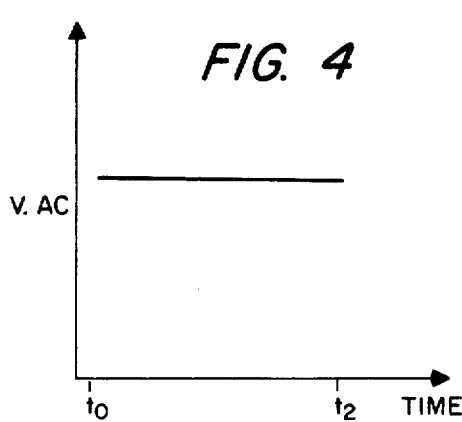
FIG. 4
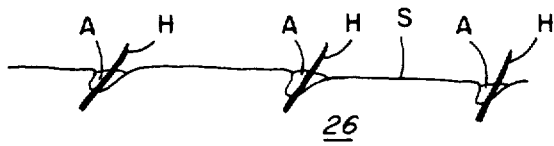
FIG. 6
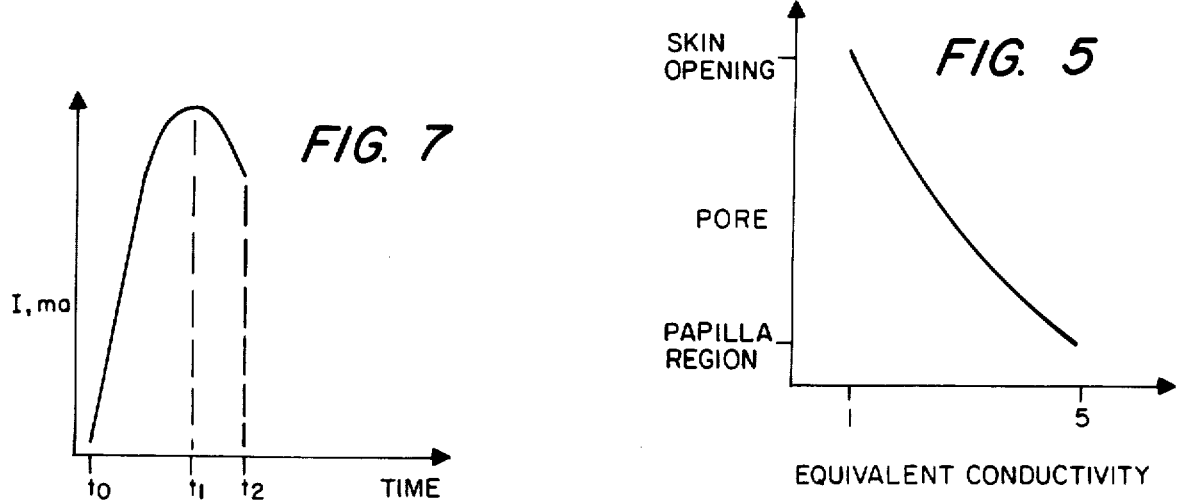
FIG. 7
FIG. 5

EPILATION METHOD

BACKGROUND OF THE INVENTION

This invention relates to epilators for removal of hair. This application is a continuation-in-part of application Ser. No. 344,494, filed Feb. 1, 1982, now abandoned which is a continuation of application Ser. No. 42,799, filed May 29, 1979, now issued as U.S. Pat. No. 4,317,450.

FIELD OF THE INVENTION

To permanently remove hair from a living being, it is necessary to stop hair growth at its source, i.e. at the papilla located at the base of the hair follicle. It is known that an electric current applied to the papilla will damage or "coagulate" the papilla and papilla connective tissue, and thus prevent it from initiating new growth. Conventional methods for applying the electric current are not reliable and often lead to painful burning of the skin and possible scarring. Two methods are presently in wide use. The oldest is referred to as electrolysis. In electrolysis an attempt is made to precisely insert a thin needle into the papilla and a controlled RF voltage (from approximately 200 to 500 volts) is applied. Skill is needed to properly locate the papilla, and improper needle insertion can be painful. Furthermore, some persons have curved or spiral hair follicles, making it especially difficult to locate the papilla.

The other conventional method, first disclosed in the Fozzard U.S. Pat. No. 2,888,927, replaces the needle with tweezers which grasps the hair above the skin. A high RF voltage up to 800 volts is then applied for a period of 6 to 45 seconds. At the end of this time, the hair is supposed to release and slide out. In practice, the method is less than 50 percent effective, and success seems to depend on the properties of the hair being removed. Under normal conditions hair is not a good conductor of electricity, thus it has been surmised that the method relies on capacitive coupling between the tweezers and the papilla.

Both conventional methods are time consuming and potentially painful should their high voltages be wrongly applied.

SUMMARY OF THE INVENTION

We have discovered a new method of removing a hair from a living being comprising the steps of applying a fluid (which can be a gel, cream, emulsion or the like, as well as a classical solution) having ionic activity and wetting characteristics for hair and surrounding skin, to the hair and surrounding skin, allowing the ionic, wetting fluid to penetrate into the follicle containing the hair, applying a regulated voltage to the vicinity of the wetted hair, and drawing the hair out of the follicle.

According to preferred embodiments of the method, the ionic fluid has an ionic activity equivalent to at least about 25 ppm sodium chloride in water solution; two or more ionic, wetting fluids are applied to the hair and surrounding skin sequentially, the last having lower ionic activity than the preceding fluid, preferably the method includes applying the preceding fluid to the hair and surrounding skin, allowing the preceding ionic, wetting fluid to penetrate into the pore containing the hair to be removed, wiping the preceding fluid from the surface of the surrounding skin in a manner to leave a deposit of fluid in the pore, applying a final ionic, wetting fluid to the hair and surrounding skin and thereafter applying the regulated voltage, and preferably the ratio of ionic activity of the preceding fluid to the ionic activity of the final fluid is in the range of about 10:1 to 1:1, more preferably the ratio is about 5:1, and the preceding fluid has an ionic activity equivalent to at least about 100 to 500 ppm sodium chloride in water solution and the final fluid has an ionic activity equivalent to at least about 25 to 150 ppm sodium chloride in water solution; the ionic activity is provided by including compounds with ion content to mass ratio higher than the ion content to mass ratio of lauryl sulfate compounds, preferably the ion content to mass ratio of said compounds is at least three times that of said lauryl sulfate compounds, and preferably the compounds providing the ionic activity include sodium chloride; the ionic, wetting fluid further comprises a buffering compound, preferably the buffering compound comprises a quaternary nitrogen compound; the wettability of the fluid is of the order of that necessary for a drop of the fluid having volume of about 1/20 ml. to spread over about 5 square centimeters of skin with a film thickness of approximately 0.1 mm; preferably the wettability characteristics of the fluid are provided by one or more long chain organic substances with ionizable end groups, more preferably the substance is selected from the following: lauryl sulfates, diethanol amines, compounds of diethanol amines, long chain organic acids, and their derivatives; the method includes applying the voltage to the hair through the tips of tweezers gripping the hair close to the surface of the skin, and drawing the hair from the follicle by means of the tweezers; the voltage is of the order of 35 to 65 VAC; the voltage is applied at a frequency of 27.120 megahertz; the application of the voltage to the wetted hair promotes penetration of the ionic, wetting fluid into the follicle to the region of the papilla connective tissue; the method includes causing the arrector muscle surrounding the hair to relax whereby movement of the fluid downwardly in the pore is facilitated, preferably the application of the voltage to the wetted hair generates a field along the hair affecting the arrector muscle to facilitate the movement of fluid; and the fluid and the regulated voltage are cooperatively related to alter papilla connective tissue to deter regrowth of papilla and hair.

In certain preferred embodiments, a preceding fluid has high detergent properties for removal of oils and the like from the skin and hair. The application and subsequent removal thereof serves to remove the oils and the like from the vicinity of the hair to be removed, whereby persons of different skin characteristics can be brought to substantially the same conditions enabling a final fluid of predetermined properties to be used across a wide population having different skin characteristics.

In another aspect of the invention, a fluid for removal of hair from a living being, for example by means of the method just described, has the combined properties of ionic activity and wetting capability when applied to the hair and surrounding skin, whereby upon application to the hair and surrounding skin the fluid has sufficient wettability to penetrate the follicle containing the hair to the region of the papilla connective tissue to effect the papilla connective tissue and regrowth of hair in the follicle.

According to preferred embodiments of this aspect of the invention, the wettability of the fluid is of the order of that necessary for a drop of fluid having volume of about 1/20 ml. to spread over about 5 square centimeters of skin, with a film thickness of approximately 0.1 mm; the wettability characteristics of the solution are provided by one or more long chain organic substances with ionizable end groups, preferably the substance is selected from the following: lauryl sulfates, diethanol amines, compounds of diethanol amines, long chain organic acids, and their derivatives; the ionic fluid has an ionic activity of at least equivalent to 25 ppm sodium chloride in water solution; the ionic activity is provided by including compounds with ion content to mass ratio higher than the ion content to mass ratio of lauryl sulfate compounds, preferably the ion content to mass ratio of the compounds is of the order of at least three times that of the lauryl sulfate compounds, and more preferably the compound providing said ionic activity is sodium chloride; the fluid further comprises a buffering compound, preferably the buffering compound comprises a quatenary nitrogen compound; the ionic activity and wetting characteristics of the fluid applied to the hair and surrounding skin are a composite of the combined ionic activities and wetting characteristic of at least two compatible fluids; the ionic, wetting fluid comprises a combination of two or more fluids applied to the hair and surrounding skin sequentially, preferably at least one of the combination of two or more fluids is a prep solution having high detergent capabilities for removing skin oils from the follicle containing the hair and the surrounding skin when wiped therefrom, and the fluid is adapted to be applied to the hair and surrounding skin preceding application of at least one other of the combinations of fluids, more preferably the prep solution has an ionic activity equivalent to at least about 100 ppm sodium chloride in solution, and preferably the combination of two or more fluids is a master solution having an ionic activity equivalent to at least about 25 ppm sodium chloride in solution and having high wetting characteristics; and the ratio of ionic activity of the prep solution to the ionic activity of the master solution is in the range of about 10:1 to 1:1, preferably the ratio is about 5:1.

According to still another aspect, the invention comprises an epilator system useful for removing a hair from a living being comprising a fluid having ionic activity and wetting characteristics for hair and surrounding skin, the fluid adapted upon application to a hair and surrounding skin to penetrate into the follicle containing the hair to the region of the papilla connective tissue, and the fluid adapted to effect the papilla connective tissue and regrowth of hair in the follicle.

In preferred embodiments of this aspect of the invention, the system is comprised of at least two fluids having ionic activity and wetting characteristics for the hair, a first fluid having high detergent capabilities for removing skin oils from the follicle containing the hair and the surrounding skin when wiped therefrom, preferably the fluids are adapted for sequential application to the hair and surrounding skin, the first fluid comprising a prep solution for initial application to the hair and surrounding skin, and the second fluid comprising a master solution for application after the prep solution, the master solution having an ionic activity level below the ionic activity level of prep solution. In this embodiment, the ratio of ionic activity of the prep solution to the ionic activity of the master solution is in the range of about 10:1 to 1:1, preferably about 5:1, the prep solution has an ionic activity equivalent to at least about 100 ppm sodium chloride in solution, and the master solution has an ionic activity equivalent to at least about 25 ppm sodium chloride in solution. In the preferred embodiments, the wettability of the fluid is of the order of that neccessary for a drop of the fluid having volume of about 1/20 ml. to spread over about 5 square centimeters of skin, with a film thickness of approximately 0.1 mm; and the system is further comprised of an electrical means adapted for applying a regulated voltage in the vicinity of the hair, the fluid and the electric means adapted to act cooperatively for removal of the hair, preferably electric means is a high frequency RF source.

PREFERRED EMBODIMENT

A preferred embodiment of the invention will now be described, after first briefly describing the drawings.

FIG. 1a is a cross-sectional view of a human hair growing in a skin follicle during the prep solution stage, FIG. 1b is a cross-sectional view of the same hair and skin follicle after initial application of the voltage showing the fluid of the invention in place around the hair both inside and outside the follicle, and FIG. 1c is a cross-sectional view of the same hair and skin follicle during removal of the hair after separation of the papilla connective tissue;

FIG. 2 is a cross-sectional top view of the hair and skin follicle taken at the line 2—2 of FIG. 1a;

FIG. 3 is a circuit schematic of the high-frequency voltage generator and a diagrammatic view of the tweezers for grasping a hair;

FIG. 4 is a plot of the voltage applied at the tip of the tweezers during a typical hair removal cycle;

FIG. 5 is a curve depicting the equivalent conductivity of the fluid along the axis of a wetted hair;

FIG. 6 is a somewhat diagrammatic side view showing a number of hair and skin follicles after the prep solution stage;

FIG. 7 is a plot of the variation in current supplied by the tweezers during a typical hair removal cycle;

Figure 8:
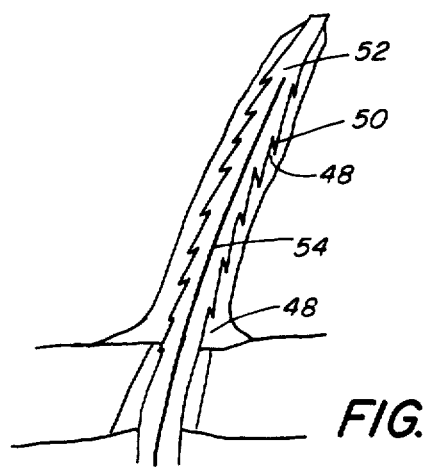
FIG. 8 is a side section view of a coarse, cuticle encased hair wetted by the fluid.
Figure 2:
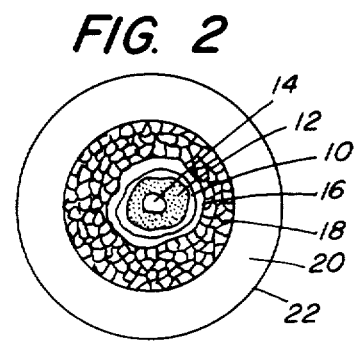

Referring to FIGS. 1a and 2, a human hair, H, grows in follicle, F, a tube-like inversion of the skin about 1.6 to 3.8 mm deep. In the region at the surface of the skin, the hair consists of three concentric shells, the cuticle 10, the cortex 12, and the medulla 14, naming them from the outer surface. The medulla, which is clusters of cells separated by intercellular spaces, has a finite conductance due to the electrolyte composition of the cytoplasm. The cortex and cuticle are largely non-conductive with a dielectric coefficient of at least three and possibly as high as ten due to the polarizability of the protein components. The larger, coarser hairs of the body typically have the high dielectric coefficient due to the relatively thick layer of the horny, scale-like cuticle, as shown in FIG. 8, discussed more fully below, and are generally removable by the previously known methods only with greater difficulty than finer hairs.

At the bottom of the follicle, the medulla 14 merges into the papilla, P, which is partly surrounded by the bulb, B, of the hair. The hair shaft is surrounded by, in the following order moving outwardly, the epidermic coat 16 (a layer of horny, scale-like cells), the dermic coat 18, the inner root sheath 20, and the outer root sheath 22. The hair shaft, H, is also surrounded by the arrector muscle 24 which constricts the pore about the hair shaft. The papilla, P, connects the hair to the body 26 through the bottom of the follicle by means of a narrow extension of the papilla connective tissue 28 containing blood vessels, V, which provide all nourishment to the hair. Damage (sometimes referred to in the art as "coagulation") to the papilla, including damage to papilla connective tissue, will prevent regrowth of hair from that follicle.

To remove hair, the wetting, i.e. detergent, ionic fluid, A, is applied, for example in a clinic or a salon, to an area where the hair has been scissor-cut to leave only short stubs. After a few seconds the area is lightly wiped to remove oil to allow the ionic, wetting fluid to wet the hair and surrounding skin and facilitate penetration into the pore. This step may be repeated as many times as necessary. After a few seconds, a second or "master" fluid, B, is applied to the hair and the surrounding skin, S. After a few seconds, long enough for the two fluids to begin mixing, the hair is grasped by tweezers 30, slight tension is applied and power is fed to the tweezers by depressing foot switch 32.

Referring to FIG. 1b, the tips 36 of tweezers 30 grasp a human hair, H, at about 1.0 to 1.6 mm above the skin level. (FIG. 1b shows the tweezers somewhat closer than 1.0 mm.)

Referring to FIG. 3, tweezers 30 are typically powered, through foot switch 32, by high-frequency (27.120 megahertz) voltage generator 34 for producing a low-power output at tweezers 30. The maximum power delivered by the tweezers is limited by the power output of the generator, which is about 1.0 watt. The generator supplies an RF voltage in the range of 35 to 80 VAC, preferably 35 to 65 VAC, when foot pedal switch 32 is closed. A plot of the voltage applied to the wetted hair is essentially constant, as shown in FIG. 4. Tweezers 30 are molded from plastic to provide insulation, and the voltage is carried to the tweezers by a coaxial cable whose length is selected to maximize power transfer to the tweezers.

Both fluids have the characteristics of ionic activity and wettability, which theoretically is measured by the angle of the tangent in the surface of the liquid at the point of contact with a solid surface. For purposes of this invention this may be sufficiently defined as follows: a drop of solution of about 1/20 ml volume spreads across about 5 square centimeters of skin to give a film thickness of about 0.1 mm. This wettability allows the fluids to work down into the follicle into the region of the papilla connective tissue. Suitable wetting agents include such water-soluble nonionized surfactants as polyoxy ethylene oleyl ether. Preferred for use in the system of this invention, however, are long chain compounds with ionizable end groups, preferably these compounds are organic, and preferably they have a mixture of valent and covalent bonds. Lauryl sulfate salts are typically used as they can satisfactorily provide both the wettability, and the ionic characteristics that are desirable.

The oiliness of skin may vary from person to person and in different areas of the body. The wettability characteristics of the fluids chosen, particularly in the prep solution, additionally contribute to the efficacy of the system by considerably decreasing the oil-water interfacial tension thereby creating a detergent effect. This removes oil from the hair surface and thereby aids in directing the RF energy into the follicle. Furthermore, the wettability of the fluids, particularly after penetration into the follicle to envelope the hair, is believed to allow the fluids to serve as a lubricant between the hair and the surrounding follicle walls to facilitate removal of the hair therefrom when tension is applied.

The prep solution has a higher ionic activity level than the master solution, typically of the order of equivalent to about 100 to 500 ppm sodium chloride in water solution versus equivalent to about 25 to 150 ppm, and preferably about 35 to 100 ppm, sodium chloride in water solution, respectively, or a ratio in the range of about 10:1 to 1:1, or preferably about 5:1. This is achieved, typically, by the use in the prep solution of a larger proportion of smaller molecules having an ion content to mass ratio at least three times higher than the ion content to mass ratio of the lauryl salt compounds, and preferably about five times higher. The remaining ion content is provided by the long chain organic compounds with a mixture of covalent and valent bonds and ionizable end groups, e.g. lauryl sulfate salts, diethanol amines, compounds of diethanol amines and certain long chain organic acids and their derivatives. Additional ionic activity is provided by the intrinsic ionization of the wetting detergent ingredients which are chosen from the readily available, inorganic-based, lauryl sulfate salts widely used in detergents due to their generally nontoxic characteristics. A buffering compound, e.g. certain quatenary nitrogen compounds chosen for nontoxicity, compatibility with other ingredients and long shelf life, may also be used in the system to maintain the fluid at the desirable pH level. It is generally preferred that the pH of the fluid be maintained essentially neutral in the pH range of about 6 to 9. The large molecules of the nitrogen quatenary compound are also believed to retard the activity of the ions in the master solution.

The wettability characteristics of both the prep solution and the master solution are compatible to allow the fluids to begin mixing in the pore, but it is believed that the ionic activity of the fluid in the follicle increases from the skin to the area of the papilla, as shown in FIG. 5, due to the sequential application of the prep and master solutions.

After application of the prep solution and wiping (FIG. 1a), a small volume 38 of the fluid remains in the pore about the hair shaft (see also, FIG. 6). Due to its wettability, a portion of the fluid is believed to work into the constricted follicle. The master solution is then applied to the hair and surrounding skin. After a short delay to allow this fluid to enter the pore, an electric charge is applied (FIG. 1b). While the actual means by which the following occurs is not fully understood, it is believed that the application of the electric charge assists the ionic fluid to penetrate the hair follicle into the region of the papilla connective tissue where desirable damage occurs to the tissue to allow removal of the hair and prevent regrowth.

It is surmised that in the presence of the ionic, wetting fluid a combination of conductance of the charge from the tweezers into the region through the ionic fluid, a capacitive coupling between the hair and the tweezers, and an electric field created by the voltage generated at 27.120 megahertz, a known medical frequency, which may also relax the constriction of arrector muscle to cause fluid to be drawn into the follicle by suction and allow easier removal of the hair (FIG. 1c), together cause the observed desirable damage to the tissue.

Further it is believed that other properties of the fluids, e.g. the high detergent characteristics or the ionic activity, once allowed to penetrate into the region of the papilla connective tissue, may also cause effects beneficial to the process.

It is further surmised that this process is the result of a synergistic effect of the above.

Conductance

The wetting fluid with ionic properties when applied to the hair creates a conductive film along the hair. The high-frequency voltage, lower than used in conventional epilators is then applied to the wetted hair.

In certain preferred embodiments, the wetting fluid is selected such that when the applied fluid is subjected to a difference in potential, the charged particles (ions) will establish a conductive path from tweezer tips, which are grasping the hair just above the skin, down to the papilla. The ionic strength of the fluid can vary, the limits being dependent to some degree on individual factors such as the natural conductivity of the hair of the user. For our purpose a good guide for selecting the current-carrying ability of the fluid is that it has a conductivity equivalent to approximately 25 ppm sodium chloride in solution. This fluid should have sufficient current-carrying capability for removal of hair from a wide range of individuals.

A typical plot of current versus time after the foot switch is depressed at time $t_0$ is given in FIG. 7. Initially, current rises rapidly to a maximum at time $t_1$ which is about 10 ma. After a brief interval of approximately 2 seconds time ($t_2$) the tweezed hair slides out under tension by the tweezers. Without further wetting, other hairs in the area can also be removed in turn until it is apparent that additional wetting is required. Removal of some hairs, for example those coarse hairs covered with a thick layer of horny, scale-like cuticle, as shown in FIG. 8, is more difficult by previously known methods. These coarse hairs are more porous to the wetting fluid than the finer hairs whose scales lie flatter, and require the particular wettability characteristics of the fluid of the invention. The wettability of fluid 48 allows it to penetrate under the cuticle scales 50 of hair 52 into the area of the more conductive living medulla 54, which allows the charge to be conducted by the hair, even in the nonconductive cuticle segment, to facilitate the hairs removal.

It is thought that the phenomena shown in FIG. 7, i.e. initial rapid current rise to a maximum at time $t_1$ (about 10 ma), current decay after a brief interval of approximately 2 seconds (time $t_2$), and a cease in the conductive interval as the treated hair is slid out under tension by the tweezers, (which provides a built-in check against burning by limiting the duration of current flow), is caused by movement of the fluid within the follicle. The follicle is normally closed around the hair. The current flow may tend to slightly warm the follicle, which opens to aid penetration of the fluid. As the fluid works down the follicle and approaches the papilla, the blood vessels, V, provide a better conductive path than do the follicle walls, and thus the current tends to increase to a maximum at $t_1$ in FIG. 7. The excellent conductive path provided by the fluid to the papilla and by the blood vessels beyond the papilla assure that a concentration of current flows through the papilla rather than the follicle walls, which are coated with oils and thus less conductive, and enough energy is supplied to the papilla to damage it. The fluid available at the surface flows into the follicle until it is depleted.

The conductivity of the path provided by the fluid along a hair will decay after a time interval of no greater than 20 seconds, preferably approximately 2 to 10 seconds, thereby limiting the amount of current flowing to the body to prevent burns. During this short interval, the fluid delivers an effective current to the region of the papilla, in all likelihood the majority of the current flowing to there rather than to the surrounding follicle wall and skin.

It is thought that the rapid decay of the current curve is the result of an interruption in the conductive path rather than a change in the chemical composition of the fluid (although the latter may be a contributing factor). The conductive path could be broken either by the papilla connective tissue being coagulated, i.e. damaged, and thus separated from the highly-conductive blood vessels or by a break or stretching out and thinning of the conductive film provided by the fluid.

Capacitive Coupling

Capacitive coupling of the tweezers and the papilla is surmised to be the method relied upon by depilatron methods, but in that field markedly higher voltages are required (800 volts versus preferably 35 to 65 in this system) with much less of the desired effect. In this invention, capacitive coupling is surmised to be a contributing factor, though much lower voltages are required, probably due to the ionic, wetting fluid.

Field

The generation of the voltage at the frequency of 27.120 megahertz is believed to generate a warming condition in the tissue of the hair follicle, with particular effect on the arrector muscle which is caused to relax its constriction about the hair shaft to allow the ionic, wetting fluid to enter into the area of the papilla connective tissue. It is surmised that the application of the electrical charge to the hair also generates, in effect, a driving force in the ionic, wetting fluid, which, it is believed, drives the highly mobile ions down into the follicle to the base of the pore where it has the desirable effect of damaging papilla connective tissue to allow the hair with the papilla to be removed. This removal also allows the fluid, I, to collect in a puddle at the base of the pore where the papilla was located, and this may have some further effect on the desirable damage done to the tissue to prevent regrowth.

Other Embodiments

Figure 9:
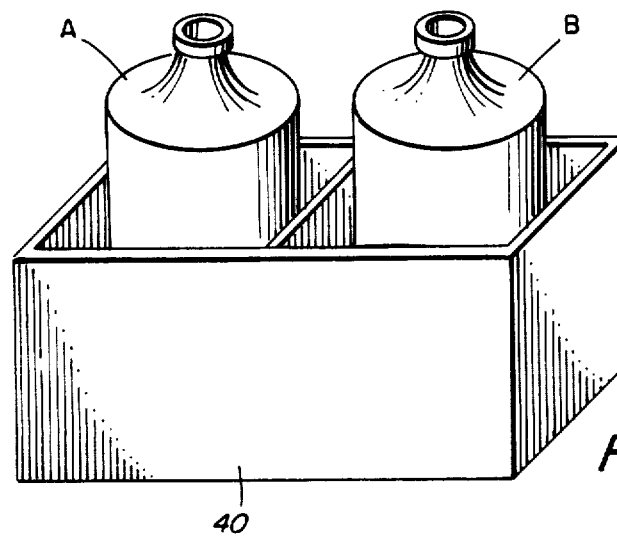
FIG. 9 is an isometric view of an epilator kit according to the invention.
Figure 10:
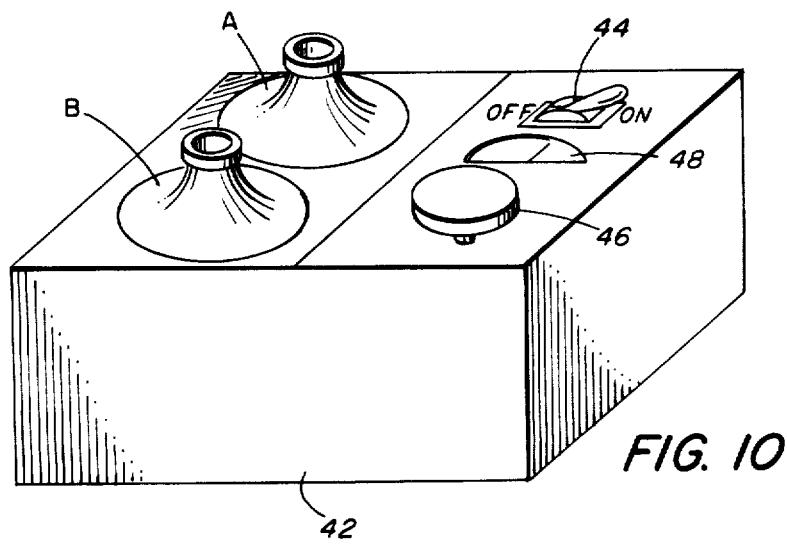
FIG. 10 is an isometric view of a powered epilator kit according to the invention.

Other embodiments of the invention are within the following claims. For example, as shown in FIGS. 9 and 10, the prep and master fluids, A and B, respectively, may be supplied in kits, 40, 42, e.g., for consumer home use. In FIG. 10, kit 42 is equipped for powered operation, e.g. AC, DC or battery, by means of switch 44 and power button 46. The power applied is monitored on meter 48. Many other fluids having the necessary wetting and ionic or conductive properties could also be substituted for the disclosed fluids, with or without application of electric current, to remove hair. Also, compatible fluids having greater or substantially less of the desirable characteristics of wettability and high ionic activity may be combined, for example on the skin, for use according to the invention. Different electrical voltage generators could be employed, or voltage from DC or a battery power supply could be applied.

The frequency of the generator might also be other than 27.120 megahertz. This frequency has been selected because it is a typical medical frequency.

What is claimed is:

1. A method of removing a hair from a living being comprising the steps of:
    applying a fluid having ionic activity and wetting characteristics for hair and surrounding skin, to the hair and surrounding skin,
    said fluid having an ionic activity equivalent to at least about 25 ppm sodium chloride in water solution,
    allowing said ionic, wetting fluid to penetrate into the follicle containing said hair,
    applying a regulated voltage to the vicinity of said wetted hair, and
    drawing said hair out of said follicle.

2. The method of claim 1 wherein two or more ionic, wetting fluids are applied to said hair and surrounding skin sequentially, the last having lower ionic activity than the preceding fluid.

3. The method of claim 2 including the step of applying said preceding fluid to said hair and surrounding skin,
    allowing said preceding ionic, wetting fluid to penetrate into the pore containing the hair to be removed,
    wiping said preceding fluid from the surface of said surrounding skin in a manner to leave a deposit of said fluid in said pore,
    applying a final ionic, wetting fluid to said hair and surrounding skin and thereafter applying said regulated voltage.

4. The method of claim 3 wherein a preceding fluid has high detergent properties for removal of oils and the like from the skin and hair, the application and subsequent removal thereof serving to remove said oils and the like from the vicinity of the hair to be removed, whereby persons of different skin characteristics can be brought to substantially the same conditions enabling a final fluid of predetermined properties to be used across a wide population having different skin characteristics.

5. The method of claim 2 wherein the ratio of ionic activity of said preceding fluid to the ionic activity of said final fluid is in the range of about 10:1 to 1:1.

6. The method of claim 5 wherein said ratio is about 5:1.

7. The method of claim 5 wherein said preceding fluid has an ionic activity equivalent to about 100 to 500 ppm sodium chloride in water solution and said final fluid has an ionic activity equivalent to about 25 to 150 ppm sodium chloride in water solution.

8. The method of claim 1 wherein the ionic activity is provided by including compounds with ion content to mass ratio higher than the ion content to mass ratio of lauryl sulfate compounds.

9. The method of claim 8 wherein the ion content to mass ratio of said compounds is at least three times that of said lauryl sulfate compounds.

10. The fluid of claim 8 wherein said compounds providing said ionic activity include sodium chloride.

11. The method of claim 1 wherein said ionic, wetting fluid further comprises a buffering compound.

12. The method of claim 11 wherein said buffering compound comprises a quatenary nitrogen compound.

13. The method of claim 1 wherein the wettability of said fluid is of the order of that necessary for a drop of said fluid having volume of about 1/20 ml. to spread over about 5 square centimeters of skin with a film thickness of approximately 0.1 mm.

14. The method of claim 13 wherein wettability characteristics of said fluid are provided by one or more long chain organic substances with ionizable end groups.

15. The method of claim 14 wherein said substance is selected from the following:
    lauryl sulfates, diethanol amines, compounds of diethanol amines, long chain organic acids, and their derivatives.

16. The method of claim 1 wherein said method includes the further steps of applying said voltage to said hair through the tips of tweezers gripping said hair close to the surface of said skin, and
    drawing said hair from said follicle by means of said tweezers.

17. The method of claim 1 wherein said voltage is of the order of 35 to 65 VAC.

18. The method of claim 1 wherein said voltage is applied at a frequency of 27.120 megahertz.

19. The method of claim 1 wherein the application of said voltage to said wetted hair promotes penetration of said ionic, wetting fluid into said follicle to the region of the papilla connective tissue.

20. The method of claim 1 wherein said method includes the further step of causing the arrector muscle surrounding said hair to relax whereby movement of said fluid downwardly in the pore is facillitated.

21. The method of claim 20 wherein the application of said voltage to said wetted hair generates a field along said hair affecting said arrector muscle to facilitate said movement of fluid.

22. The method of claim 1 wherein the fluid and the regulated voltage are cooperatively related to alter papilla connective tissue to deter regrowth of papilla and hair.

* * * * *